United States Patent [19]

Homandberg et al.

[11] Patent Number: 4,892,826

[45] Date of Patent: Jan. 9, 1990

[54] PROCESS FOR THE PREPARATION OF UROKINASE DERIVATIVES

[75] Inventors: Gene A. Homandberg, Evanston; Thanda Wai, Libertyville, both of Ill.

[73] Assignee: Abbott Laboratories, Abbott Park, Ill.

[21] Appl. No.: 255,681

[22] Filed: Oct. 11, 1988

[51] Int. Cl.$^4$ ............................................. C12N 9/00
[52] U.S. Cl. .................................... 435/183; 435/212; 435/215
[58] Field of Search ........................ 435/212, 215, 183

[56] References Cited

U.S. PATENT DOCUMENTS

| | | | |
|---|---|---|---|
| 4,326,033 | 4/1982 | Holleman | 435/215 |
| 4,349,630 | 9/1982 | Maximenko | 435/215 |
| 4,525,465 | 6/1985 | Someno | 435/215 |
| 4,536,391 | 8/1985 | Miyozaki | 435/215 |
| 4,545,988 | 10/1985 | Nakayama | 435/215 |

OTHER PUBLICATIONS

Robbins et al., Biochemistry, 25, 3603–3611 (1986), "Covalent Molecular Weight 92,000 Hybrid Plasminogen Activator Derived from Human Plasmin Amino-Terminal and Urokinase Carboxyl-Terminal Domains".

Sumi et al., Journal of Biological Chemistry, 258, 8014–8019 (1983), "A Functionally Active Heavy Chain Derived from Human High Molecular Weight Urokinase".

Winkler and Blaber, Biochemistry, 25, 4041–4045 (1986), "Purification and Characterization of Recombinant Single–Chain Urokinase Produced in *Escherichia coli*".

Maksimenko et al., Thrombosis Research, 38, 277–288 (1985), "Water–Soluble Urokinase Derivatives of Combined Action".

Maksimenko et al., Thrombosis Research, 38, 289–195 (1985), "Water–Soluble Urokinase Derivatives with Increased Affinity to the Fibrin Clot".

*Primary Examiner*—Peter D. Rosenberg
*Attorney, Agent, or Firm*—Steven F. Weinstock; Rae K. Stuhlmacher; Andreas M. Danckers

[57] ABSTRACT

A process for making urokinase derivatives having a sulfhydryl group incorporated into a remnant of urinary plasminogen activator. The process comprises reducing disulfide bridges in the presence of arginine and incorporating a desired compound having a sulfhydryl containing group into the structure through the formation of a disulfide bridge.

13 Claims, No Drawings

PROCESS FOR THE PREPARATION OF UROKINASE DERIVATIVES

TECHNICAL FIELD

This invention relates to a new process for the preparation of urokinase derivatives.

BACKGROUND OF THE INVENTION

The clotting process follows a series of autocatalytic reactions eventually forming fibrin, the insoluble protein network which forms the essential portion of the blood clot. The blood clot is first formed from fibrin, which subsequently entangles other blood components such as platelets, white cells, and red cells to form an aggregate. This aggregation of blood components is referred to as a thrombus and the formation, development, or presence of a thrombus is referred to as thrombosis.

Fibrin is formed from fibrinogen by the proteolytic action of thrombin, an enzyme derived from prothrombin, during the normal clotting of blood. When vessels or body cells are damaged, a prothrombin activator is released that converts the prothrombin into thrombin. The thrombin, in the presence of several accessory factors, converts soluble fibrinogen into insoluble fibrin. For example, the rupture of a blood vessel can create a roughened surface to which platelets adhere and partially plug the break. This initiates the development of a prothrombin activator. The prothrombin activator converts prothrombin to thrombin. The thrombin can then convert the fibrinogen to fibrin, the insoluble protein network forming the blood clot. After the function of the clot has been fulfilled, fibrin is normally digested into soluble products.

Plasmin is the active portion of the thrombolytic, or clot-lysing, system and has a high specificity for fibrin. Plasminogen, present in the blood, is converted to plasmin in a reaction that is catalyzed by plasminogen activators such as urinary plasminogen activator (u-PA).

The high molecular weight form of human urinary activator has one kringle domain, or region of sequence homology, with a relatively low fibrin-binding affinity. Pennica et al., Nature (London), 301, 214–221 (1983). Effectively, the human high molecular weight urinary activator, urokinase (UK1), displays no specific affinity to fibrin or fibrinogen.

The native, or naturally occurring, human high molecular weight UK1 is a serine protease that is synthesized in the kidney and excreted into the urine. Two major molecular forms of UK1 have been isolated from human tissues and characterized; a high molecular weight form with a molecular weight of approximately 54,000 daltons, and a low molecular weight form with an approximate molecular weight of 31,000 daltons. The high molecular weight UK1 is considered to be the major native form found in urine and the low molecular weight form of UK1 is considered to be an enzymatically degraded form of the high molecular weight UK1. Both forms have been found to contain two chains linked by a disulfide bond. Hiroyuki et al., J. Biol. Chem., 258, 8014–8019 (1983). The $NH_2$-terminal, or A chain, has a single kringle domain that shows extensive homology with the plasminogen kringles, whereas the active center of the enzyme is located in the COOH-terminal, or B chain. Robbins et al., Biochemistry, 25, 3603–3611 (1986).

Nonnative forms of urokinase are collectively described herein as UK2. The high molecular weight urokinase, UK1, can be cleaved between Lysine (Lys) and Isoleucine (Ile), which are located in positions 158 and 159, respectively, as conventionally determined from the $NH_2$ terminus of the urokinase molecule, to form a two-chain urokinase ($UK2_1$). The two chains are held together by a single disulfide bond which is located between Cysteine (Cys), in position 148, and Cys, in position 279. This form, $UK2_1$, is more active toward chromogenic substrates than the high molecular weight form, UK1; however, it also displays increased plasminogen binding. Lijnen et al., J. Biol. Chem., 261, 1253–1258 (1986); Collen et al., J. Biol. Chem., 261, 1259–1266 (1986). A smaller version, $UK2_2$, can be formed by cleaving the high molecular weight form of urokinase after Lys, in position 135.

In another version, $UK2_3$, the molecule begins at Leucine (Leu), in position 144 as numbered in the high molecular weight UK1, and is missing the two amino acids Phenylalanine (Phe) and Lys, in positions 157 and 158, respectively. Similarly, the two chains are held together by a single disulfide bond between Lys and Ile, which are located in positions 158 and 159, respectively. The two chains include a short A chain, having the 13 residue peptide from positions 144 to 156, and a long B chain beginning at position 159, having the COOH-terminal at about position 411 and containing the active center of the enzyme. The 13 residue peptide is referred to herein as the remnant A peptide and has the amino acid sequence Leu-Lys-Phe-Glu-Cys-Gly-Glu Lys-Thr-Leu-Arg-Pro-Arg. The $UK2_3$ form of urokinase is available commercially and is sold by Abbott Laboratories under the registered trademark "ABBOKINASE".

The UK2 forms of urokinase retain the single kringle domain found in the much larger A chain of high molecular weight UK1 as well as the active center that is located in the COOH terminal, or B chain. Similarly, the UK2 forms of urokinase have no specific affinity to fibrin or fibrinogen.

Current clinical therapies for dissolution of blood clots that occur in myocardial infarction, deep vein thrombosis and pulmonary embolism, often involve the use of UK2 to activate the fibrinolytic system in blood. This systemic activation can cause degradation of fibrinogen and lead to a decrease in circulating plasminogen, as well as other clotting factors. Verstraete, Fibrinolysis, 185–200, CRC Press, Boca Raton, FL (1980). Plasminogen is converted to the active enzyme plasmin. When plasmin circulates freely in the blood it promotes systemic activation, thus, degrading a number of proteins, including fibrinogen. The systemic activation of plasminogen is due to the specific binding affinity of urokinase for plasminogen, wherever found, and the lack of specificity for fibrin that is found at the site of the blood clot. Verstraete, *Fibrinolysis*, 185–200, CRC Press, Boca Raton, FL (1980). An overt systemic fibrinolytic state and very low fibrinogen levels can occasionally lead to major bleeding. Collen et al., Thrombolysis, 74, 838–842 (1986).

It is desirable, therefore, to incorporate synthetic peptides having specific clot binding properties into the u-PA type of urokinase in order to provide fewer systemic complications and reduce the likelihood of major bleeding.

Prior art attempts have been made to impart clot binding properties to urokinase derivatives. The catalytic carboxyl-terminal domain of residues of UK was combined with the amino-terminal plasmin kringle region recovered from reduced plasmin. A mixture of the two components was allowed to oxidize and the hybrid was isolated. Robbins et al., Biochemistry, 25, 3603-3611 (1986).

Sumi et al., Journal of Biological Chemistry, 258, 8014-8019 (1983), reported the mild reduction and carboxymethylation of high molecular weight urokinase (UK1) with 2-mercaptoethanol to generate two chains, a functionally active heavy chain and a light chain. This process reduced only one connecting disulfide bridge.

An E. coli expressed recombinant high molecular weight single-chain urokinase was expressed and refolded using a glutathione catalyzed system. Winkler and Blaber, Biochemistry, 25, 4041-4045 (1986). This reduction-reoxidation procedure was slow, requiring up to 48 hours in the presence of guanidine, and resulted in a low yield.

Maksimenko et al., Thrombosis Research, 38, 277-288 (1985), generated a heparin-urokinase derivative by carbodiimide promoted coupling of heparin to non-reduced low molecular weight urokinase.

Maksimenko et al., Thrombosis Research, 38, 89-295 (1985), generated another urokinase derivative by attachment of fibrinogen through a spacer of an aliphatic diamine to carbodiimide activated low molecular weight two-chain urokinase.

DISCLOSURE OF THE INVENTION

The present invention relates to a process for making urokinase derivatives. In a limited reduction system, the remnant A peptide (the 13 residue remnant of the two-chain urokinase molecule which is numbered 144 to 156 in high molecular weight urokinase) of the urokinase, previously identified and defined as $UK2_3$, is first removed and a desired sulfhydryl containing compound, such as a sulfhydryl containing synthetic A peptide, as defined herein is oxidized back onto the structure.

For convenience in describing this invention, the conventional abbreviations for the various common amino acids are used as generally accepted in the peptide art.

| Amino Acid | Three-letter Symbol | One-letter Symbol |
|---|---|---|
| Alanine | Ala | A |
| Arginine | Arg | R |
| Asparagine | Asn | N |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Threonine | Thr | T |
| Valine | Val | V |

As used herein, the term "parent urokinase molecule" refers to a low molecular weight urokinase molecule having a large catalytically active polypeptide chain linked by a single disulfide bond to a small non-catalytic remnant peptide chain (A). The parent urokinase exemplified herein is $UK2_3$, previously defined as beginning at Leucine (Leu), in position 144 as numbered in the high molecular weight UK1, and missing the two amino acids Phe and Lys, in positions 157 and 158, respectively. The two chains are held together by a single disulfide bond between Lys and Ile, which are located in positions 158 and 159, respectively. The two chains include a short A chain, having the 13 residue peptide from positions 144 to 156, and a long B chain which begins at position 159 and has the COOH-terminal at about position 411.

As used herein, the term "sulfhydryl containing compound" or "compound having a sulfhydryl containing group" refers to a compound having at least one SH group such as thiol compounds, cysteine containing peptides or proteins, as well as sulfhydryl containing peptides. The sulfhydryl containing compounds can be naturally occurring or can be synthesized by any of the techniques that are known to those skilled in the art.

As used herein, the term "synthetic peptide" refers to a sulfhydryl containing peptide which exhibits a desired characteristic, for example, a specific clot binding capacity for components found in the human blood clot.

The term "synthetic peptide" is utilized herein to illustrate that it is the synthetic A peptide that replaces the remnant A peptide which is released from the urokinase molecule As used herein, the term "reducing agent" refers to recognized reducing agents for proteins and enzymes as employed in biochemical reactions, such as Cleland's reagent. Such reducing agents are readily ascertained by one of ordinary skill in the art and include, among others, mercaptoethanol and dithiothreitol (DTT). Preferably, DTT is employed as the reducing agent in the present invention.

The synthetic peptides of the present invention can be synthesized by any techniques that are known to those skilled in the art. For solid phase peptide synthesis, a summary of the many techniques can be found in J. M. Stewart and J. D. Young, *Solid Phase Peptide Synthesis*, W. H. Freeman Co., San Francisco (1963). For classical solution synthesis, see G. Schroder and K. Lupke, *The Peptides*, vol. 1, Academic Press, New York (1965).

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

A particularly preferred method of preparing the synthetic peptides of the present invention involves solid phase peptide synthesis. Using this method, the alpha-amino function of the amino acid is protected by an acid or base sensitive group. Such protecting groups should have the properties of being stable to the conditions of peptide linkage formation, while being readily removable without destruction of the growing peptide chain or racemization of any of the chiral centers contained therein. Suitable protecting groups are t-butyloxycarbonyl (BOC), benzyloxycarbonyl (Cbz), biphenylisopropyloxycarbonyl, t-amyloxycarbonyl, isobornyloxycarbonyl, (alpha,alpha)-dimethyl-3,5 dimethoxybenzyloxycarbonyl, o-nitrophenylsulfenyl, 2 cyano t-butyloxycarbonyl, 9 fluorenylmethyloxycarbonyl and the like. The BOC protecting group is preferred.

In the solid phase peptide synthesis method, the C-terminal amino acid is attached to a suitable solid support. Suitable solid supports useful for this synthesis are those materials which are inert to the reagents and reaction conditions of the stepwise condensation-deprotection reactions, as well as being insoluble in the media used. For example, suitable solid supports can include chloromethylpolystyrene-divinylbenzene polymer, hydroxymethyl-polystyrene-divinyl benzene polymer, and the like.

The coupling of successive protected amino acids can be carried out in an automatic polypeptide synthesizer as is well known in the art. The removal of the alpha-N-protecting groups can be performed in the presence of, for example, a solution of trifluoroacetic acid in methylene chloride, hydrogen chloride in dioxane, hydrogen chloride in acetic acid, or other strong acid solution. Each protected amino acid is preferably introduced in 0.4M concentration in approximately 3.5 molar excess and the coupling can be carried out in dichloromethane, dichloromethane/DMF mixtures, DMF and the like, especially in methylene chloride at about ambient temperature. The coupling agent can include DCC in dichloromethane, N,N'-di-isopropylcarbodiimide (DLIC) or other carbodiimide either alone or in the presence of HOBt, N-hydroxysuccinimide, other N-hydroxyimides or oximes, as well as symmetrical anhydrides.

At the end of the solid phase synthesis, the fully protected polypeptide is removed from the resin. When the linkage to the resin support is of the benzyl ester type, cleavage is by means of aminolysis with an alkylamine of fluoroalkylamine for peptides with a proline C-terminus, or by aminolysis with, for example, ammonia/methanol or ammonia/ethanol for peptides with a glycine C-terminus at a temperature of between about 10 degrees C. to about 50 degrees C. Alternatively, the peptide can be removed from the resin by transesterfication, e.g., with methanol, followed by aminolysis or by direct transamidation. The protected peptide can be purified at this point by silica gel chromatography or taken to the next step directly. The removal of the side chain protecting groups from the polypeptide is performed by treating the aminolysis product with, for example, anhydrous liquid hydrogen fluoride in the presence of anisole and dimethylphosphite or other carbonium scavenger. The hydrogen fluoride treatment is carried out at a temperature of between about $-10$ degrees C. and about $+10$ degrees C. for between about 15 minutes and 1 hour.

The fully deprotected polypeptide can be purified by a sequence of chromatographic steps employing any or all of the following types: ion exchange on a weakly basic resin in the acetate form; hydrophobic adsorption chromatography on underivatized polystyrene-divinylbenzene (for example Amberlite XAD); silica gel adsorption chromatography; ion exchange chromatography on carboxymethylcellulose; partition chromatography, e.g., on Sephadex G-25, LH-20, or countercurrent distribution; and high performance liquid chromatography (HPLC), especially reverse phase HPLC on octylor octadecylsilyl silica bonded phase column packing.

Generally, the parent $UK2_3$ is diluted with arginine and reduced. An excess of synthetic A peptide is added to the system and the reaction is allowed to proceed to incorporate the synthetic A peptide into the urokinase molecule. Thereafter, the urokinase derivative can be isolated.

The parent $UK2_3$, in a buffered solution, is diluted with from about 70 mM to about 250 mM of arginine, an amount sufficient to maximally saturate the urokinase molecule. As will be explained in greater detail, the addition of the arginine stabilizes the urokinase molecule and protects against over-reduction of the disulfide bridges.

From about 1 mM to about 25 mM, more preferably from about 2.5 mM to about 20 mM, of a reducing agent is added to the system to reduce three of the five available urokinase disulfide bridges. As will be discussed in greater detail, the outcome of the urokinase derivative process is independent of the concentration of the reducing agent over a range of from about 1 mM to about 25 mM. In other words, increasing the concentration of the reducing agent will increase the rate of reduction of the urokinase but will not effect the resulting urokinase derivative.

When three of the five available disulfide bridges have been reduced, usually 2 to 4 hours, the reducing agent can be removed, for example by dialysis utilizing Spectrapor 6(1000 MWCO) dialysis tubing. As the reducing agent is removed, two of the disulfide bridges oxidize and the structure refolds to a native conformation. The step of refolding to a native conformation contributes to the formation of the correct disulfide bridges and is necessary to impart the desired biological affinity to the urokinase derivative.

After the reducing agent is removed, the sulfhydryl containing compound, such as a synthetic A peptide, is added to the system and the reaction is allowed to proceed to form the desired urokinase derivative. The extent of disulfide bridge reduction can be determined, for example, by monitoring the amidolytic activity of the urokinase. The amidolytic activity toward the tripeptide urokinase chromogenic substrate L-pyroglutamylglycyl-L-arginyl-p-nitroanilide (S-2444) will decrease during reduction due to the reduction of disulfide bridges and increase during the removal of the reducing agent due to the reformation of disulfide bridges. The amidolytic activity of the reduced $UK2_3$ is preferably allowed to decrease to from about 5% to about 25% of the value of the amidolytic activity of the parent $UK2_3$, more preferably to from about 15% to about 25%, and most preferably to about 20% of the value of the amidolytic activity of the parent $UK2_3$ When the amidolytic activity of the reduced $UK2_3$ has dropped to from about 5% to about 25% of the value of the amidolytic activity of the parent $UK2_3$, three of the five disulfide bridges will have been reduced.

Alternatively, the urokinase is reduced in the presence of arginine until the amidolytic activity has dropped to from about 5% to about 25% of the amidolytic activity of the parent $UK2_3$, and the synthetic A peptide is added at the beginning of, or during, the dialysis procedure.

A 15 to 30 molar excess, preferably a 30 molar excess, of the synthetic A peptide, as compared to the parent urokinase concentration, is added to the system. A 30 molar excess of the synthetic A peptide is preferred to maximize the collision frequency of the synthetic A peptide with the reduced urokinase and maximize the recovery of the urokinase derivative. The urokinase derivative can be isolated after approximately one hour, for example, by application to a column containing a molecular sieve material such as a gel filtration resin. A suitable molecular sieve material is a Sephadex gel of the type G-75 which has been equilibrated with 0.1M phosphate, pH 7.

Commercial preparations of $UK2_3$ can be further purified, for example, by adsorption to p-aminobenzamidine-Spharose as described in Holmberg et al., Biochim. Biophys. Acta, 445, 215–222. (1976). The protein is adsorbed to columns equilibrated with 0.4M NaCl/0.1M phosphate (pH 7.0), and eluted with 0.4M NaCl, 0.1M sodium acetate, pH 4.0. Additionally, it was found that $UK2_3$ that had been stored at 9 degrees C for several months provided a derivative having a lower amidolytic activity after the reduction and oxidation steps. On the other hand, the use of $UK2_3$ that had been freshly isolated and stored frozen, provided a urokinase derivative having an amidolytic activity of over 80%.

The specific buffer employed is not critical and is readily ascertained by one of ordinary skill in the art. Buffers that can be employed include, for example, sodium acetate, EDTA, phosphate, and the like. Neutral buffers have less of an effect on the conformation, and hence the stability, of the protein structure than low pH or high pH buffers. Further, reductions are generally considered by those skilled in the art to be more effective at a neutral pH. Therefore, it is preferred to employ a buffer having a pH range of from about 5.0 to about 8.0 and more preferred to employ a buffer, such as phosphate, having a pH of about 7.

Arginine is utilized to stabilize the urokinase molecule which will limit the disulfide reduction to three disulfide bridges. Increasing the concentration of the reducing agent will increase the rate of the remnant A peptide release, however, arginine operates to slow the peptide release in parallel with the loss of the remnant A peptide at any given concentration of reducing agent. Further, it has been found that where arginine is not utilized, there is no appreciable regain of amidolytic activity of urokinase following reduction.

The optimal concentration of arginine can be approximated by its apparent Ki value for inhibition of urokinase as calculated from a Dixon plot. Dixon, M, Biochem. J., 55, 170–171 (1953). Utilizing the tripeptide urokinase chromogenic substrate L-pyroglutamylglycyl-L-arginyl-p-nitroanilide (S 2444), the apparent Ki value is 70 mM (regression coefficient, r, is 0.98 for 7 points). A concentration at or above the apparent Ki value of 70 mM is the minimal concentration required to saturate the urokinase molecule. It is preferred that the concentration of arginine chosen will maximally saturate the urokinase molecule and confer a protective effect against the previously discussed over reduction of the disulfide bridges. Therefore, the desired concentration of arginine is from about 70 mM to about 250 mM, and preferably about 250 mM.

Increasing the concentration of the reducing agent will increase the rate of reduction of the urokinase molecule and the rate of release of the remnant A peptide. For example, solutions of urokinase (1 mg/ml) in phosphate buffer (pH 7) adjusted to concentrations of from 1 mM to 20 mM DTT in the presence of arginine indicate that increasing the concentration of DTT will increase the rate of the peptide release. However, as noted previously, the loss in amidolytic activity in the presence of arginine occurs in parallel with the loss of the remnant A peptide at varying concentrations of the reducing agent. Therefore, varying the concentration of the reducing agent will result in the reduction of only three out of the five possible disulfide bridges, although the reduction will take place at different rates.

The reduction of the three disulfide bridges can be monitored, for example, by assays of the amidolytic activity of the urokinase, by titration of the available SH groups, or by reverse phase chromatography of the reduced urokinase. Preferably, the reduction is monitored by assaying the gain or loss of amidolytic activity of the urokinase. Urokinase amidolytic activity can be assayed by mixing 0.1 ug to 1 ug of urokinase and 10 ul of 10 mM S-2444 substrate in an assay buffer (50 mM Tris, 100 mM NaCl, pH 7.4, at ambient temperature) according to Hayashi et al., Thromb. Res., 22, 573–578 (1981). Utilizing this method, $UK2_3$ was found to have an average activity of 125 u/ug. When the amidolytic activity has dropped to from 15% to 25% of the initial urokinase value, usually 2 to 4 hours, three of the five available disulfide bridges will have been reduced.

The reducing agent is then removed from the system. Preferably, the solution is dialyzed to remove the reducing agent utilizing, for example, Spectrapor 6 (1000 MWCO) dialysis tubing. It is most preferred that the solution is dialyzed against two changes of 100 volumes of 0.1M phosphate, 0.2M arginine, pH 7 for about 90 to 100 minutes for each of the dialysis steps. During this time, the amidolytic activity will have increased to a value of from approximately 70% to approximately 80% of the initial $UK2_3$ value. This amidolytic activity increase is due to the reformation of two of the disulfide bridges and the refolding of the molecule into a native conformation. However, the state of oxidation can be monitored by other methods, such as reverse phase chromatography.

When the amidolytic activity has increased to approximately 70% to 80% of the initial value of the parent urokinase, the synthetic A peptide, which like the remnant A peptide must contain at least one sulfhydryl group, is added in approximately a 15 to 30 molar excess over the parent urokinase. A 30-fold excess is preferred to maximize the collision frequency of the catalytic chain with the synthetic peptide.

The urokinase derivative can be isolated after approximately one hour. For example, the solution can be applied to a gel filtration resin, such as Sephadex G-75, or any other gel filtration resin having similar performance characteristics.

The composition of the urokinase derivative is confirmed by protein sequencing. Generally, the polypeptide is separated into amino acid subunits, or sequences, and those subunits are identified, for example, by HPLC analysis. In this case, the urokinase derivatives were confirmed by automated Edman degradation. In the Edman procedure phenylisothiocyanate reacts quantitatively with the free amino group of a peptide to yield the corresponding phenylthiocarbamoyl peptide. On treatment with anhydrous acid the N-terminal residue is split off as a phenylthiocarbamoyl amino acid, leaving the rest of the peptide chain intact. The phenylthiocarbamoyl amino acid is then cyclized to the corresponding phenylthiohydantoin derivative, which can be separated and identified, for example by gas or liquid chromatography. Alternatively, the N-terminal residue which is removed as the phenylthiocarbamoyl derivative, can be identified simply by determining the amino acid composition of the peptide before and after removal of the N terminal residue. This is the subtractive Edman method. The Edman procedure can be performed in an automated sequencer such as the automated sequencer manufactured by Applied Biosystems, Inc., Models 470A or 477.

The foregoing can be better understood from the following examples, which are presented for the purposes of illustration and are not intended to limit the scope of the inventive concepts.

EXAMPLE 1

GPRP-Amino hexanoic acid-LKFQCGQK Urokinase Derivative

The 1-13 residue A chain remnant of $UK_{23}$ was removed and replaced with a synthetic A peptide, which includes GPRP, the fibrin binding region of the amino terminus of the alpha chain of fibrinogen, coupled through amino-hexanoic acid to an eight residue peptide sequence, LKFQCGQK.

(a) Purification of UK2 3.

Freshly isolated $UK_{23}$ (obtained from Abbott Laboratories) was purified by adsorption to p-aminobenzamidine-Sepharose columns eguilibrated with 0.4M NaCl, 0.1M phosphate, pH 7.0; and eluted with 0.4 M NaCl, 0.1M sodium acetate, pH 4.0. Holmberg et al., Biochim. Biophys. Acta, 445, 215-222 (1976).

(b) Synthesis of the synthetic A peptide.

The synthetic A peptide was prepared using a solid phase peptide synthesis method, as discussed previously, employing an automatic polypeptide synthesizer (Applied Biosystems 430A Peptide Synthesizer). BOC-protected amino acids were employed for the coupling reactions. BOC-Arg(tosyl), BOC-Cys(4-CH 3 benzyl), BOC-Lys(Cl-carbobenzoxy) and BOC-Thr(benzyl) were utilized for the incorporation of Arg, Cys, Lys, and Thr, respectively. The peptides were assembled starting with a BOC-aminoacyl polystyrene resin and the coupling proceeded with two couplings of each amino acid utilizing symmetrical anhydride. For Arg and Glu, a double coupling program was followed utilizing hydroxy benzotriazole esters. The peptides were removed from the resin and treated with anhydrous liquid HF/anisole (9:1, 1 hour) to remove the side chain protecting groups. The resins were washed with ethyl acetate/diethyl ether (1:1, 100 mL per gram of resin) and the peptides were extracted with 10% acetic acid in water and lyophilized. The composition of the peptide was determined by amino acid analysis of hydrolyzates (6 N HCl, 110 degrees C., 24 hours) on an amino acid analyzer, such as the Beckman 6300 Amino Acid Analyzer, and were found to have amino acid compositions which corresponded to the desired sequence.

(c) Incorporation of the synthetic A peptide GPRP-Amino hexanoic acid-LKFQCGQK, containing one cysteine-SH residue Approximately 1 to 2 mg/ml of the $UK_{23}$ solution, in 0.1M phosphate (pH 7), was diluted with 1 volume of 0.5M arginine in water (pH 7). The reducing agent DTT, from a fresh stock solution of 1M in water, was added to adjust the final DTT concentration to 10 mM. The amidolytic activity toward the amidolytic substrate S-2444 was assayed by mixing from 0.1 ug to 1 ug of either the $UK_{23}$, the reduced $UK_{23}$, or the $UK_{23}$ derivative, and 10 uL of 10 mM S-2444 substrate in assay buffer (50 mM Tris, 100 mM NaCl, pH 7.4, at ambient temperature). The absorbance increase at 406 nm was monitored over a five minute period. One enzyme unit was defined as an increase in absorbance at 406 nm of 1 unit per minute. $UK_{23}$ was found to have an average activity of 125 u/ug.

When the monitored amidolytic activity of the reduced $UK_{23}$ had decreased to approximately 20% of the initial $UK_{23}$ value, the reduction solution was dialyzed, utilizing Spectrapor 6 (1000 MWCO) dialysis tubing, at ambient temperature against 100 volumes of 0.1M phosphate, pH 7, containing 0.2M arginine for about 90 minutes. Thereafter, the dialysis buffer was changed and the reduction solution was dialyzed with a fresh dialysis buffer for an additional period of about 90 minutes. After the second dialysis, the solution was found to be free of detectable DTT, as measured by DTNB (Ellman's SH reagent) titration of the dialysate. Further, the amidolytic activity was found to have increased to a value of from 55% to 65% of the initial $UK_{23}$ value and the structure of the urokinase molecule was found to have refolded to a native configuration (as shown by the characteristic retention time of the native protein on a reverse-phase C-4 HPLC column).

The synthetic A peptide GPRP-Amino hexanoic acid-LKFQCGQK, containing one cysteine-SH residue, was then added such that there was a 30-fold molar excess of synthetic A peptide over the concentration of the $UK_{23}$. The reaction was allowed to proceed for approximately 1 hour. The urokinase derivative was then isolated and purified by application of the sample to a 1.5×90 cm Sephadex G-75 molecular sieve gel filtration column that had been eguilibrated with 0.1M phosphate (pH 7). The derivative was found to elute in the position of native urokinase and was devoid of excess peptide, as shown by a reverse phase chromatography HPLC analysis utilizing a C-4 peptide/protein column and a gradient of from 90% water, 0.1% (v/v) TFA/10% acetonitrile to 40% water, 0.1% (v/v) TFA/60% acetonitrile at 1%/minute and 1 ml/minute at ambient temperature.

Repeated procedures were performed as indicated above. The derivatives were recovered in a 70% to 80% yield and were found to have an amidolytic activity of between 80% to 100% of the initial $UK_{23}$ value.

EXAMPLE 2

GPRP-Amino hexanoic acid-LKFQCGQK Urokinase Derivative

In the described fashion as Example 1, $UK_{23}$ was reduced in the presence of 10 mM DTT and 250 mM arginine until the amidolytic activity dropped to 0%. The synthetic A peptide GPRP-Amino hexanoic acid-LKFQCGQK was then added and the dialysis begun. The title compound was recovered in a 75% yield

EXAMPLE 3

GAGDV-Amino-hexanoic acid-LKFQCGQK Urokinase Derivative

Following the procedure of Example 1 and employing the synthetic A peptide GAGDV-Amino-hexanoic acid-LKFQCGQK provided the desired title compound.

EXAMPLE 4

Heparin-LKFQCGQK Urokinase Derivative

Following the procedure of Example 1 and employing a heparin-LKFQCGQK synthetic A peptide provided the desired urokinase derivative.

The heparin-LKFQCGQK synthetic peptide was prepared by coupling heparin to the peptide structure LKFQCGQK. To a 1 ml solution of 150 mg of heparin in 1 M pyridine-HCl (pH 5) was added 25 mg of carbodiimide at 9 degrees C. After 10 minutes, a 1.0 ml solution of 1 mM of the peptide LKFQCGQK in 1M pyridine HCl buffer was added to the reaction. After 24 hours at 9 degrees C, the solution was dialyzed, utilizing Spectrapor 6(1000 MWCO) dialysis tubing, against four changes of 1000 volumes of water. The yield of the coupled peptide was calculated from the absorbance at 257 nM (absorbance found in Phe) and from the disappearance of the peptide peak as measured by HPLC reverse phase chromatography analysis and found to be 75%. The reverse phase chromatography analysis was performed on a 0.46×25 cm Vydac C-4 peptide/protein column (Rainin Instrument Co., Woburn, MA) and developed with a gradient of 90% water, 0.1% (v/v) TFA/10% acetonitrile to 40% water, 0.1% (v/v) TFA/60% acetonitrile at 1%/minute and ambient at temperature.

The resulting derivative had an apparent molecular weight of about 60,000 (Sephadex G 75 column) and was 100% active.

EXAMPLE 5

AAHEEICTNEGVM-Amino-hexanoic acid-LKFQCGQK Urokinase Derivative

In the described fashion as Example 1, a collagen binding urokinase derivative can be made by replacing the synthetic A peptide with a peptide containing the collagen-binding region of human plasma fibronectin. The collagen-binding synthetic peptide is prepared by coupling the collagen-binding region of human plasma fibronectin to the peptide structure LKFQCGQK.

EXAMPLE 6

GPRP-Amino-hexanoic acid-Cys Urokinase Derivative

Following the procedure of Example 1 and employing a GPRP-Amino hexanoic acid-Cys synthetic A peptide provided the desired urokinase derivative.

EXAMPLE 7

GPRP-Amino-hexanoic acid Amino-hexanoic acid-Cys Urokinase Derivative

Following the procedure of Example 1 and employing a GPRP-Amino-hexanoic acid-Amino-hexanoic acid-Cys synthetic A peptide provided the desired urokinase derivative.

It will be understood that various changes and modifications can be made in the details of the procedure to adapt it to various conditions without departing from the spirit of the invention. Upon further study of the specification and the appended claims, further objects and advantages of this invention will become apparent to those skilled in the art. Those skilled in art will appreciate that the process of the present invention is applicable to sulfhydryl (SH) containing compounds other than the synthetic A peptides specifically described herein. For example, the process of the present invention is similarly applicable to the incorporation of thiol compounds, cysteine containing peptides or proteins, or sulfhydryl containing peptides which can display an affinity for components other than fibrin, such as collagen.

What is claimed is:

1. A process for the preparation of urokinase derivatives, the process comprising:
   (a) saturating a parent urokinase molecule with arginine;
   (b) reacting the saturated parent urokinase molecule in arginine with an amount of reducing agent sufficient to reduce the parent urokinase molecule to a reduced urokinase molecule by reducing three disulfide bridges;
   (c) removing the reducing agent; and
   (d) reacting the reduced urokinase molecule with from at least about 15 to about 30 molar excess of a desired compound having a sulfhydryl containing group.

2. The process as defined in claim 1 wherein the compound having a sulfhydryl containing group is a synthetic peptide.

3. The process as defined in claim 2 wherein the synthetic peptide is GPRP-Amino hexanoic acid-LKFQCGQK.

4. The process as defined in claim 2 wherein the synthetic peptide is GAGDV-Amino-hexanoic acid-LKFQCGQK.

5. The process as defined in claim 1 wherein the compound having a sulfhydryl containing group is added before the reducing agent is removed, in step (c).

6. The process as defined in claim 1 wherein the compound having a sulfhydryl containing group is added in at least about 30 molar excess of the compound having a sulfhydryl containing group over the urokinase molecule.

7. The process as defined in claim 1 wherein the arginine is added at a concentration range of from at least about 70 mM to about 250 mM of arginine.

8. The process as defined in claim 1 wherein the reducing agent is dithiothreitol.

9. The process as defined in claim 1 wherein the reduction step further comprises monitoring the reduction of the disulfide bridges by assaying the amidolytic activity of the reduced urokinase molecule against the tripeptide urokinase chromogenic substrate L-pyroglutamylglycyl-L-arginyl-p-nitroanilide as compared to the amidolytic activity of the parent urokinase molecule against the same substrate.

10. The process as defined in claim 9 wherein the reduction of the disulfide bridges is monitored until the amidolytic activity value of the reduced urokinase reaches a value of from about 5% to about 25% of the value of the unreduced parent urokinase molecule and thereafter removing the reducing agent.

11. The process as defined in claim 1 wherein the single peptide chain Leu-Lys-Phe-Glu-Cys-Gly-Glu-Lys-Thr-Leu-Arg-Pro-Arg is removed from the parent urokinase molecule.

12. A process for the preparation of urokinase derivatives, the process comprising:
   (a) saturating a parent urokinase molecule with and a B chain wherein the parent urokinase molecule begins with Leucine, in position 144 as numbered in a high molecular weight native urokinase molecule, and is missing the two amino acids Phenylalamine and Lysine, in positions 157 and 158, respectively, and wherein the A chain includes, from positions 144 to 156, the amino acid sequence Leu-Lys-Phe-Glu-Cys-Gly-Glu-Lys-Thr-Leu-Arg-Pro-Arg, and wherein the B chain begins at position 159 and includes the COOH-terminal, the two chains being held together by a single disulfide bond between Lysine and Isoleucine, in positions 158 and 159, respectively;

(b) reacting the saturated parent urokinase molecule in arginine with an amount of reducing agent sufficient to reduce the parent urokinase molecule to a reduce urokinase molecule by reducing three disulfide bridges;

(c) removing the reducing agent; and (d) reacting the reduced urokinase molecule with from at least about 15 to about 30 molar excess of a desired synthetic peptide.

13. The process as defined in claim 12 wherein the synthetic peptide is added before the reducing agent is removed, in step (c).

* * * * *

UNITED STATES PATENT AND TRADEMARK OFFICE
CERTIFICATE OF CORRECTION

PATENT NO. : 4,892,826
DATED : January 9, 1990
INVENTOR(S) : Gene A. Homandberg, Thanda Wai It is certified that error appears in the above-identified patent and that said Letters Patent is hereby corrected as shown below:

Column 2, line 15, replace "UK22" with --UK2$_2$--; line 31, add a hyphen between "Glu" and "Lys".

Column 3, line 23, replace "89-295" with --289-295--.

Column 6, line 58, after "UK2$_3$" add --.--.

Column 7, line 54, replace "(S 2444)" with --(S-2444)--.

Column 9, line 26, replace "UK2 3 ." with --UK2$_3$.--.

Column 10, line 57, replace "0%" with --20%--.

Column 11, line 29, replace "G 75" with --G-75--.

Column 12, line 64, after "with" add --arginine, the parent urokinase molecule having both an A chain--.

Signed and Sealed this

Fifth Day of February, 1991

Attest:

HARRY F. MANBECK, JR.

*Attesting Officer*  *Commissioner of Patents and Trademarks*